(12) United States Patent
Kjær (10) Patent No.: US 11,937,612 B2
(45) Date of Patent: Mar. 26, 2024

(54) IMAGING BASED PORTION CUTTING (71) Applicant: MAREL SALMON A/S, Stovring (DK)

(72) Inventor: Anders Kjær, Aabybro (DK)

(73) Assignee: MAREL SALMON A/S, Stovring (DK)

( * ) Notice: Subject to any disclaimer, the term of this patent is extended or adjusted under 35 U.S.C. 154(b) by 335 days.

(21) Appl. No.: 17/427,533

(22) PCT Filed: Feb. 6, 2020

(86) PCT No.: PCT/EP2020/052972
§ 371 (c)(1),
(2) Date: Jul. 30, 2021

(87) PCT Pub. No.: WO2020/161229
PCT Pub. Date: Aug. 13, 2020

(65) Prior Publication Data
US 2022/0095631 A1     Mar. 31, 2022

(30) Foreign Application Priority Data

Feb. 6, 2019 (EP) .................................. 19155756

(51) Int. Cl.
*A22C 17/00* (2006.01)
*A22C 25/18* (2006.01)
(Continued)

(52) U.S. Cl.
CPC ........ *A22C 17/0086* (2013.01); *A22C 17/002* (2013.01); *A22C 25/18* (2013.01);
(Continued)

(58) Field of Classification Search
CPC ............ A22C 17/0086; A22C 21/0023; A22C 17/002; A22C 25/18; G65G 43/08;
(Continued)

(56) References Cited

U.S. PATENT DOCUMENTS 4,576,071 A    3/1986   Rayment
5,980,377 A *  11/1999  Zwanikken .............. A22B 7/00
                                                   452/158
(Continued)

FOREIGN PATENT DOCUMENTS

WO    2006108690 A2    10/2006
WO    2006108690 A3    10/2006

OTHER PUBLICATIONS

Search Report and Written Opinion from corresponding EP Application No. 19155756.0, dated Jul. 17, 2019.
(Continued)

*Primary Examiner* — Richard T Price, Jr.
(74) *Attorney, Agent, or Firm* — Workman Nydegger (57) ABSTRACT

A food processing system and method for cutting a food item into cut food item portions includes a conveyor, an imaging system, a cutting device, and a controller. The conveyor conveys the food item past the imaging system allowing the imaging system to image the food item and image data is obtained. The controller receives the imaging data and determines the location of defective areas on the basis thereof. Then a distribution of portion cuts over the food item dividing the food item into food item portions is determined on the basis of at least the determined location of defective areas and a desired portion size and/or weight. The cutting device cuts the food item according to the determined distribution of portion cuts.

21 Claims, 2 Drawing Sheets

(51) Int. Cl.
*B65G 43/08* (2006.01)
*G01N 33/12* (2006.01)
*A22C 21/00* (2006.01)
*B07C 5/342* (2006.01)

(52) U.S. Cl.
CPC ............. *B65G 43/08* (2013.01); *G01N 33/12* (2013.01); *A22C 21/0023* (2013.01); *B07C 5/342* (2013.01); *B65G 2201/0202* (2013.01); *B65G 2203/0208* (2013.01); *B65G 2203/041* (2013.01)

(58) Field of Classification Search
CPC ... G65G 2203/0208; G65G 2201/0202; G65G 2203/041
USPC ......................................................... 452/155

See application file for complete search history.

(56) References Cited

U.S. PATENT DOCUMENTS

| | | | | |
|---|---|---|---|---|
| 6,198,834 | B1* | 3/2001 | Belk | G01N 33/12 |
| | | | | 382/110 |
| 7,404,759 | B2* | 7/2008 | Sato | A22B 5/0041 |
| | | | | 452/157 |
| 7,841,264 | B2* | 11/2010 | Kim | B26D 7/018 |
| | | | | 83/13 |
| 8,387,522 | B2* | 3/2013 | Rusko | B26D 5/02 |
| | | | | 99/485 |
| 9,983,572 | B2 | 5/2018 | Pfarr et al. | |
| 2018/0027848 | A1 | 2/2018 | Blaine et al. | |
| 2019/0000094 | A1 | 1/2019 | Hjalmarsson et al. | |
| 2023/0079393 | A1* | 3/2023 | Sigurgardarsson | A22C 25/08 |

OTHER PUBLICATIONS

International Search Report and Written Opinion from PCT Application No. PCT/EP2020/052972, dated Apr. 29, 2020.

* cited by examiner

IMAGING BASED PORTION CUTTING

TECHNICAL FIELD

The present invention relates to the field of food item processing, and in particular to a method of cutting a food item into food item portions by taking defective areas of the food item into consideration and use of a food item processing system for cutting a food item into cut food item portions.

BACKGROUND

Various systems are known for cutting food items. Cutting of a food item may be desired for trimming away parts of the food item that are not desired in food item products for, e.g., human consumption. Specialised automatic and semi-automatic systems exist for such purposes.

A different type of systems is directed towards cutting a food item into desired food item portions. The food item to be cut by such a system may already have been processed to at least partly remove undesired parts thereof by manual or automated trimming. Such processing helps to reduce the amount of processing and quality control needed for the food item portions having been cut. However, defects in the form of, e.g., a bruise, melanosis, haematoma may exist in the food item to be cut. Such defects may have gone undetected during previous food item processing steps or they may be a result of the previous processing steps. Whatever the reason for the defects, the defects may become part of the cut food item portions. This leads to a need for quality control of the cut food item portions and a need to discard food item portions with defects. Often such quality control requires costly manual labour and leads to wasted food.

SUMMARY

In a first aspect, embodiments of the invention provide a method of cutting a food item into food item portions by taking defective areas of the food item into consideration, the method comprising the steps of:
  a) receiving image data of the food item;
  b) determining the location of defective areas in and/or on the food item on the basis of at least the received data; and
  c) determining a distribution of portion cuts over the food item dividing the food item into food item portions on the basis of at least the determined location of defective areas and at least one portion feature;
  d) cutting the food item into food item portions according to the determined distribution of portion cuts.

In a second aspect, embodiments of the invention provide use of a food processing system for performing the method of cutting a food item into food item portions by taking defective areas of the food item into consideration.

In a further aspect, embodiments of the invention provide a food processing system comprising:
  at least one conveyor;
  an imaging system;
  a cutting device; and
  a controller in data communication with the imaging system and the cutting device, wherein the at least one conveyor is arranged to convey a food item past the imaging system and past the cutting device, and wherein the controller is configured to:
    receive data from the imaging system;
    determine the location of defective areas of the food item on the basis of at least the received data;
    determine a distribution of portion cuts over the food item dividing the food item into food item portions on the basis of at least the determined location of defective areas and a desired portion size and/or weight; and
    controlling the cutting device based on the distribution of portion cuts.

In another aspect, embodiments of the invention provide a method of cutting a food item into food item portions by use of a food processing system, the food processing system comprises a conveyor, an imaging system, a cutting device, and a controller, the method comprising the steps of:
  the conveyor conveying the food item past the imaging system;
  the imaging system imaging the food item and obtaining image data thereof;
  the controller:
    receiving the image data;
    determining the location of defective areas on the basis of at least the received data; and
    determining a distribution of portion cuts over the food item dividing the food item into food item portions on the basis of at least the determined location of defective areas and a desired portion size and/or weight;
  the cutting device cutting the food item according to the determined distribution of portion cuts.

In the description of embodiments of the invention it is to be understood that processes described in relation to a feature of a processing system, such processes may also be included in a method.

Thanks to the provision of the cutting device cutting the food item into cut food item portions based also on the location of defective areas in the food item, the number of food item portions containing defects may be reduced. This is because the cutting device controlled in this manner is effectively able to cut out areas containing defects. When the cutting device cuts the food item without taking account of defective areas, the cutting device may very well cut the food item in a defective area thereby creating two cut food item portions containing defects. Accordingly, embodiments of the invention allow for optimised yield of cut food item portions. When cutting close to a defect in a leading part and also close to the rear part of a defect, such as cutting across a food item similar to performing a portion cut, such a part with a defect may look like a food portion and being a 'defect-containing portion', though preferably it is sorted out, and may be used for other purposes such as minced meat.

In present context, the term 'defect' or 'defective' is to be understood as an undesired part which is not inherently expected in all food items, this may be organic defects in the food item, such as, e.g., a bruise, abscess, worm, nematode, blood spot, gaping (texture opening), melanosis (melanin spots), and/or haematoma (blood cloths). Accordingly, a defect is in the present context not bone, tendon or fat tissue of meat, nor is it the seed or stem of fruit, or foreign bodies, such as metal or plastic. For processing of fish such as Salmon the preferred defects to use when determining portion cuts are blood spots, melanin spots and/or gaping of the fish meat.

In determining a distribution of portion cuts over the food item, portion cuts may be determined close to located defective areas, and preferably not into or through defective areas. 'Close to defective areas' may mean just beside an area with a defect, such as 0.1 mm from an outline of the defect, e.g. within 0.2 mm, 0.3 mm, 0.4 mm or 0.5 mm from an outline of the defect, though 'close to' may also be determined in accordance to the size of defect-free areas located next to a defect-containing area and where the defect-free areas are determined to be cut into e.g. fixed weight. In such a situation to obtain defect-free portions of the determined weight cuts 'close to' defects may be at a distance above 0.5 mm from an outline of a defect. When determining a distribution of portion cuts over the food item, portion cuts may be determined in areas without defective areas and which cuts may further be determined on the basis of at least one portion feature.

The at least one portion feature may be selected from the group of: portion size, portion weight, portion shape, portion colour, portion colour distribution, portion meat texture and/or portion meat-fat ratio.

Also a step of detecting a colour distribution of the food item can be included as an embodiment, and determining the location of the defective areas based on at least the colour distribution.

Further, by determining the location of defects prior to cutting the food item, the need for quality control of the cut food item portions is reduced. This is because information on which cut food item portions contain defective areas and which portions do not may readily be stored in the determined distribution of portion cuts. This information is then available for streamlining the process of manual, semi-automatic or fully automatic separation of cut food item portions containing defects from those that do not. The system may also comprise means for marking cut for item portions containing defects for later identification. Accordingly, the effectivity of post-cutting processing and handling may also be increased by embodiments of the present invention.

Cut food item portions containing defective areas may as described just above be separated from the defect-free cut food item portions. Those having defective areas may, e.g., be packed together and sold as they are albeit with a lower quality ranking than the defect-free portions. This allows for making use of the defect containing portions with a minimum of post-cutting processing. The defective-containing portions may also be further processed for, e.g., cutting out the defect or grinding the portion.

In some embodiments of the invention, the food item is a piece of meat from an animal such as, e.g., a fish, poultry or a mammal e.g. pig or cattle. Fish may be e.g. salmon, trout, tilapia, cod, whiting, haddock, hake, pollock. In one embodiment, the food item is a fish fillet, preferably a salmon fillet.

According to embodiments of the invention, the controller may be configured to determine the location of the defective areas in a number of different ways. For instance, the controller may have access to stored image data of known defective areas of a food item, e.g., of a particular type. The stored image data may be stored locally in a memory unit of the controller or stored externally and accessed by the controller via a network connection. The controller may execute algorithms with image recognition capabilities and compare the data received from the imaging system with the stored data, identifying similarities and discrepancies between the two sets of data. The algorithms may also comprise sets of optical parameters characteristic of typical shapes and/or colours of defects and defective areas. A match between such a stored characteristic parameter and a parameter obtained by analysis of the image data is then an indication of the presence of a defect or defective area in the imaged food item. The algorithms may have been trained by comparing provided image data with stored image data on food items known to have or not to have defective areas. The predictions of the algorithm may then be evaluated to address the accuracy of its predictions. The parameter set of the algorithm is then allowed to change after an incorrect answer, the parameter set changing towards one that would have let to a correct answer. Such training can be continued until a satisfactory level of certainty is reached.

The imaging system may be configured to image the food item in the visible light spectrum, and the control system configured to determine the location of defective areas on the basis of at least image data in the visible spectrum. This is particularly useful when a main concern is to provide visually appealing cut food item portions.

The cutting device may, e.g., be a cutting knife, a sword blade cutter, a water yet cutter, or a laser cutter. The cutting device may be located to cut in between two conveyor belts transporting the food item to be portioned, such as cutting transverse to the transporting direction and cutting food items in the entire dimension when passing from one conveyor belt to the other conveyor belt. Hereby defective areas may be cut by cutting 'defect-containing portions' i.e. pieces of food cut in similar manner as when cutting the defect-free portions. Cutting transversely to the transporting direction and along the entire width of the food item is preferred when cutting fish fillets, e.g. of salmon.

'defect-containing portion' may be removed from the conveyor e.g. by making a short-term opening between two running conveyor belts to direct the 'defect-containing portion' in between the ends of the two conveyor belts. Such opening and closing between two conveyor belts may be performed at the location where the cutting is performed, or at a location downstream the cutting.

The imaging system may comprise cameras with optical sensors, X-ray emitters and sensors, and/or ultrasonic emitters and sensors. Preferably the imaging system comprises cameras with optical sensors. In embodiments the image data of the food items is preferably obtained by the use of light, such as visible light e.g. white light, e.g. laser light, which may be a laser light line projected across the food item under transport i.e. the laser light in such a situation reaching across at least part of the conveyor surface, hereby the light source is a line light source, and may be a laser light line source which is transverse to the transport direction line of a food item. The light source may also be e.g. LED or halogen. In specific embodiments X-ray sources and X-ray cameras are preferably not used for obtaining image data.

In some embodiments, the imaging system, the at least one conveyor and the cutting device are arranged in one single device for improved compactness. In some embodiments, the imaging device and the at least one conveyor are comprised in a first device separate from a second device comprising the cutting device and at least one conveyor, which allows for retro-fitting or fitting an imaging system according to the present invention to an existing cutting device.

The at least one conveyor may comprise an in-feed conveyor conveying the food item past the imaging system and towards the cutting device. The at least one conveyor may further comprise an out-feed conveyor arranged to convey the cut food item portion away from the cutting device. The in-feed conveyor and out-feed conveyor may be arranged in an end-to-end arrangement defining a cutting plane therebetween, the cutting device being arranged to cut the food item in the cutting plane.

In some embodiments, the method comprises a step of sorting the cut food item portions, wherein the sorting is based at least on the determined distribution of portion cuts and the determined location of defective areas. Also, the system may further comprise a sorting apparatus arranged downstream of the cutting device, wherein the controller is configured to control the sorting apparatus based at least on the determined distribution of portion cuts and the determined location of defective areas for effective and automated sorting of the cut food item portions. This has the further advantage that the sorting apparatus need not itself comprise means for locating defective areas as this information is already available in the controller.

The sorting apparatus may be any suitable sorting apparatus capable of sorting out 'defect containing portions' from a food item cut into portions. Such a sorting apparatus may be a gap between two conveyor belts, where one of the conveyor belts is moved away from the other conveyor belt such that a 'defect containing portions' can enter through this gap and where the gap is closed again such that the next portion is transported from one to another conveyor belt. Sorting may also be performed manually by operators.

In some embodiments, the controller is configured to define at least a first defect level threshold defining a measure of the number and/or size of defects tolerable for a given type of food item.

Threshold values may also be values present in the system such as permanent values or values which can be into the system, such as through a computer/monitor being connected to the processor. Threshold values may be selected in respect of the quality which the food item should comply with. Examples of threshold values may be the length and/or width of a spot or the size (=area) of defects, such as length, width and/or size of blood spots, melanin spots and/or gaping texture. Examples for threshold values for e.g. blood spots and melanin spots can be set at a length or width of 10 mm and for gaping texture a length of 20 mm and a width of 5 mm. These values may be used e.g. when processing fish fillets e.g. of salmon, and when transported on a conveyor belt 'head first' or 'tail first', 'length' of the defects are determined parallel to the transport direction and 'width' perpendicular to the transport direction. The definition of the first threshold allows for a predefined tolerance level for defective areas in different kinds of food items for added versatility of the food processing system. One type of food items, e.g., salmon meat may have a different defect tolerance level than a second type of food item, e.g., veal in the eyes of the consumer. Present embodiments allow taking account of such differences leading to less waste and/or a higher product value.

In some embodiments, the food item portions of the distribution comprise at least a first group and a second group, the first group comprising food item portions having a determined defect level below a first threshold, and the second group comprising food item portions having a determined defect level above the first threshold, and wherein the size of the items in the second group are determined based on the desired portion size and/or weight of portions in the first group. According to these embodiments, the size of the portions in the second group is determined to optimize the yield of portions in the first group. This allows for an optimised yield leading to less waste.

The cutting into portions is performed by optimizing the use of non-defect areas of the food. The food item portions of the distribution may also be based on predetermined portion features, which may be e.g. weight. For salmon such weight may be e.g. 100 g, 125 g, 140 g, 160 g though different weights may also be predetermined. Also portions of variable weight may be included in the process. Hereby in parts of the food item not cut due to a defect, portion cuts may be determined due to the predetermined weights, hereby a part of a e.g. 260 g may be cut into portions of 100 g and 160 g if these portion weights are within the predetermined weights.

The cutting of the food item may be performed in accordance with the determined distribution of portion cuts over the food item and where the location of each of these cuts can be determined as a distance from a leading edge of the food item to be cut. The processor and the controller are configured to determine based on e.g. the speed of a conveyor belt when to cut, and the controller hereby controls the cutting device to cut the determined portion cuts over the food item.

The imaging system is preferentially arranged upstream of the cutting device for an optimised flow of food items.

In some embodiments, the imaging system is configured to detect a colour distribution of the food item, and the controller is configured to determine the location of the defective areas based on at least the colour distribution. By analysing colour data in contrast to, e.g., black and white data, the information richness is increased. This allows for more detailed analysis and possibly a higher success rate for identifying defective areas. When using colour distribution for determining portion cuts, defects may be determined based on colours which differ from the item's normal colour. In salmon such differing colours may be dark spots e.g. blood spots, which can have a solid structure and be circular or longitudinal. Also, in salmon melanin spots occur, which are due to amendment of the pigment colour of the meat, and the spots may be from white to black and even red. Melanin spots may be e.g. circular or longitudinal, and look dotted when zoomed in on it. Gaping is a texture defect where the meat has a loose structure. Gaping in salmon may occur because of incorrect handling of the fish or fillet.

In some embodiments the method comprises a step of determining total weight, weight distribution and/or density distribution of the food item at least partly on the basis of the received data. In some embodiments, the controller is configured to determine a two-dimensional weight distribution of the food item, the two-dimensional weight distribution extending in a plane parallel to a supporting conveyor surface of the conveyor, and to determine the distribution of portion cuts on the basis of the determined weight distribution of the food item. This allows for relatively simple determination of the distribution of portion cuts on the basis of at least a desired portion weight. The two-dimensional weight distribution may be determined on the basis of, e.g., stored data from an earlier weighing with planar resolution or on the basis of image data on the food item.

In some embodiments, the controller is configured to determine a three-dimensional surface profile of the food item on the basis of at least data received from the imaging system. This may include that the two-dimensional weight distribution is determined at least on the basis of the three-dimensional surface profile. Accordingly, the system may be self-contained in the sense that it contains the elements needed to determine the distribution of portion cuts. Also, determination of the weight distribution on the basis of at least the three-dimensional surface profile generated from the image data is a particularly efficient way of determining the weight distribution and accordingly the distribution of portion cuts.

In some embodiments, the controller is configured to determine a two- or three-dimensional density profile of the food item, and to determine the two-dimensional weight distribution of the food item on the basis of at least the determined density profile. By knowing a density profile of the food item, a more accurate distribution of portion cuts can be determined.

A method of cutting a food item such as fish fillets e.g. from salmon, into food item portions by taking defective areas of the food item into consideration may be a fully automatic method and may comprise the steps of:
a) transporting food items on a conveyor belt;
b) directing the food items past an imaging system and receiving image data of the food item;
c) determining by a processor the location of defective areas in and/or on the food item on the basis of at least the received data;
d) determining by the processor a distribution of portion cuts over the food item dividing the food item into food item portions on the basis of at least the determined location of defective areas and at least one portion feature, such as weight of the portions;
e) cutting by a cutting device controlled by a controller the food item into food item portions and defect-containing portions according to the determined distribution of portion cuts, where the cutting is performed transverse to the transport direction and across the entire food item;
f) sorting defect-containing portions from the food item portions i.e. from defect-free portions and
g) obtaining food item portions free of defects or having defects below a selected threshold value, which portions may be directed for further processing or packaging.

In the method threshold values for defective areas are preferably entered into the system before initialising the system and the method and where these threshold values are selected in respect of the quality to obtain the food item portions.

When cutting fish fillets, these are preferably transported 'head first' or 'tail first', and the food item portions are cut transverse to the length of the fillet.

BRIEF DESCRIPTION OF THE DRAWINGS

Embodiments of the invention will now be further described with reference to the accompanying drawings, in which.

DETAILED DESCRIPTION OF VARIOUS EMBODIMENTS

Figure 1:
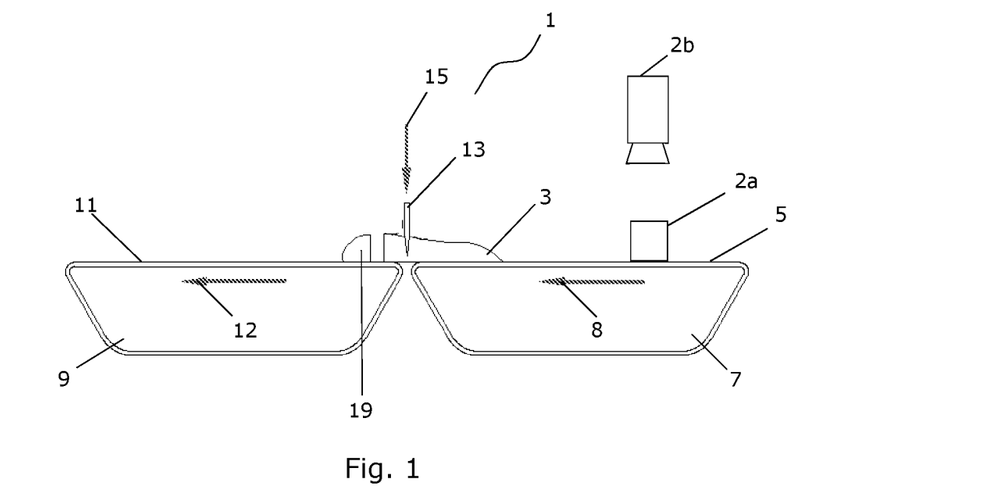
FIG. 1 is a cross sectional side view illustration of a food processing system according to the invention.

FIG. 1 illustrates a food processing system 1 according to an embodiment of the invention. The system 1 comprises an imaging system 2a, 2b arranged to image a food item 3 conveyed on the conveying surface 5 of an infeed conveyor 7 in the direction indicated by the arrow 8. The imaging system comprises an in-plane optical sensor 2a arranged to image the food item 3 transversely of the conveying direction to obtain a side view of the food item 3. The in-plane sensor 2a may also comprise, e.g., X-ray and/or ultra sound transducers. The imaging system further comprises an out-of-plane optical sensor 2b arranged to image the food item 3 from above. A controller (not shown) wirelessly receives image data of the imaged food item 3 from the imaging system 2a, 2b. The image data is analysed and the location of defective areas 20 (see FIGS. 2 and 3) is determined. The controller is also configured to determine a three-dimensional surface profile of the imaged food item 3 on the basis of a comparative analysis of the in-plane and out-of-plane image data. The controller has access to a desired portion weight (alternatively or additionally a desired portion size) and based on the desired portion weight and the location of defective areas 20, it determines a distribution of portion cuts 23 (see FIG. 3) across the food item 3.

The infeed conveyor 7 is arranged in an end-to-end arrangement with an outfeed conveyor 9 defining a conveyor surface 11 and conveying direction in the direction of the arrow 12. A cutting knife 13 (other cutting devices may be used) is arranged to cut the food item 3 in a cutting plane indicated by arrow 15 between the infeed and outfeed conveyors 7, 9. The cutting knife 13 is controlled by the controller to cut the food item 3 into cut food item portions 19 according to the determined distribution of portion cuts 23 (see FIG. 3).

Figure 2:
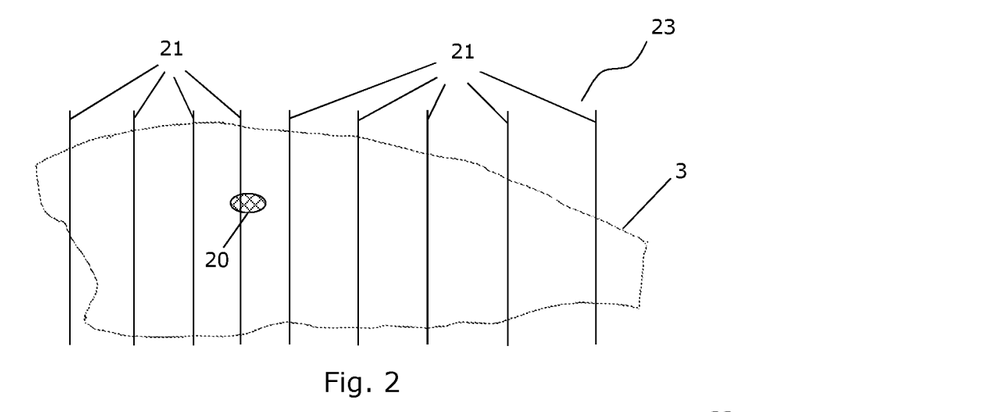
FIG. 2 is a cross sectional top view illustration of a prior art distribution of portion cuts.
Figure 3:
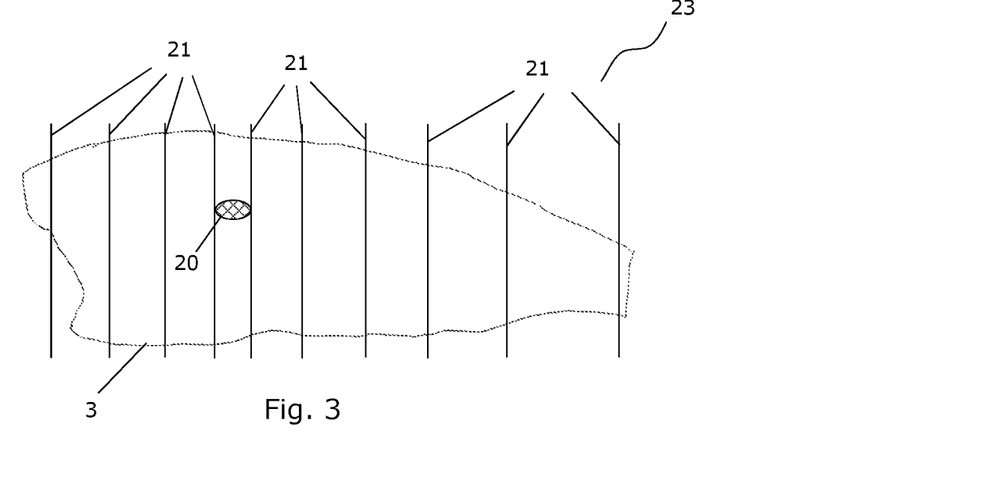
FIG. 3 is a cross sectional top view illustration of an embodied distribution of portion cuts.

FIGS. 2 and 3 illustrate cross sectional top views of distributions of portion cuts 23 across a food item 3. The food item 3 contains a defective area 20. The distribution of portion cuts 23 illustrated in FIG. 2 is not determined on the basis of the location of the defective area 20 and coincidentally a portion cut is places across the location of the defective area 20. As the cutting knife 13 would cut the food item 3 in accordance with such a distribution, the defective area 20 would be divided into two cut food item portions 19. On the other hand, the distribution of portion cuts 23 as illustrated in FIG. 3 is determined also on the basis of the location of the defective area 20. The portion cuts 21 are arranged to cut out a part containing the defective area 20 and to distribute portion cuts 21 on the basis of the desired portion weight in a way that optimises the size of defect-free cut food item portions 19. Preferably the cuts performed to obtain the defect in one 'defect-containing portion' are made close to the defect on both 'sides' of the defect when determined according to a transport direction, and such cuts are preferably made parallel to or similar to portion cuts. Accordingly, more defect-free cut food item portions 19 are obtained from the same food item 3 when being cut in accordance with the distribution of portion cuts 23 determined according to embodiments of the invention.

Figure 4:
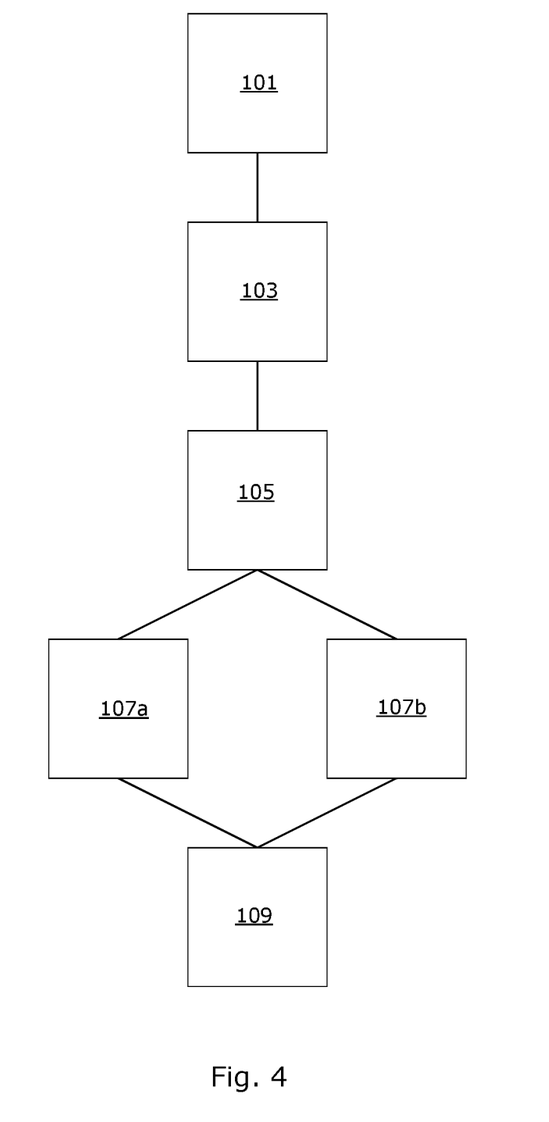
FIG. 4 is a flow chart illustrating the steps of an embodied method.

FIG. 4 is a flow-chart illustrating the steps of an embodied method of cutting a food item 3 into food item portions 19 by use of a food processing system 1. In a first step 101 an imaging system 2a, 2b of the food processing system 1 images a food item 3 as a conveyor 7 and conveys the food item 3 past the imaging system 2a, 2b.

An optional second step 103 entails determining a three-dimensional surface profile of the food item 3 on the basis of data received from the imaging system 2a, 2b, and determining a two-dimensional weight distribution on the basis of the three-dimensional surface profile.

In a second step 105, a controller of the system 1 determines the location of defective areas 20 on the basis of the received data. This can be done by executing algorithms with image recognition capabilities and comparing the data received from the imaging system 2a, 2b with the stored data, identifying similarities and discrepancies between the two sets of data. The algorithms preferably comprise sets of optical parameters characteristic of typical shapes and colours of defects and defective areas. A match between such a stored characteristic parameter and a parameter obtained by analysis of the image data is then an indication of the presence of a defect or defective area in the imaged food item.

If no defective areas are located in step 105, a distribution of portion cuts 23 is determined on the basis of e.g. desired portion size and/or portion weight in 107*a*, and, optionally, on a determined two-dimensional weight distribution, to optimize the number of cut food item portions 19 with the desired portion size and/or portion weight. If on the other hand defective areas 20 are identified and their locations determined in step 105, the distribution of portion cuts 23 is determined on the basis of the location of the defective areas 20, the desired portion size and/or weight, and, optionally, on a determined two-dimensional weight distribution in step 107*b*.

Finally, in step 109 the cutting device 13 of the system 1 cuts the food item 3 into cut food item portions 19 according to the determined distribution of portion cuts.

FIG. 4 may also be a flow-chart illustrating purely the steps of an embodied method of cutting a food item 3 into food item portions 19. In a first step 101 image data of the food item is received such as when a food item 3 is conveyed.

An optional second step 103 entails determining a three-dimensional surface profile of the food item 3 on the basis of the received image data and determining a two-dimensional weight distribution on the basis of the three-dimensional surface profile.

In a second step 105, determination of the location of defective areas 20 is performed on the basis of the received image data. This can be done by executing algorithms with image recognition capabilities and comparing the received image data with stored data, identifying similarities and discrepancies between the two sets of data. The algorithms preferably comprise sets of optical parameters characteristic of typical shapes and colours of defects and defective areas. A match between such a stored characteristic parameter and a parameter obtained by analysis of the image data is then an indication of the presence of a defect or defective area in the imaged food item.

If no defective areas are located in step 105, a distribution of portion cuts 23 can be determined on the basis of e.g. a desired portion size and/or portion weight in 107*a*, and, optionally, on a determined two-dimensional weight distribution, to optimize the number of cut food item portions 19 with the desired portion size and/or weight. If on the other hand defective areas 20 are identified and their locations determined in step 105, the distribution of portion cuts 23 is determined on the basis of the location of the defective areas 20, the desired portion size and/or portion weight, and, optionally, on a determined two-dimensional weight distribution in step 107*b*.

Finally, in step 109 the food item is cut into cut food item portions 19 according to the determined distribution of portion cuts.

EMBODIMENTS

Embodiment 1. A food processing system comprising:
at least one conveyor;
an imaging system;
a cutting device; and
a controller in data communication with the imaging system and the cutting device,
wherein the at least one conveyor is arranged to convey a food item past the imaging system and past the cutting device, and wherein the controller is configured to:
receive data from the imaging system;
determine the location of defective areas of the food item on the basis of at least the received data;
determine a distribution of portion cuts over the food item dividing the food item into food item portions on the basis of at least the determined location of defective areas and a desired portion size and/or weight; and
control the cutting device based on the distribution of portion cuts.

Embodiment 2. A system according to embodiment 1, further comprising a sorting apparatus arranged downstream of the cutting device, and wherein the controller is configured to control the sorting apparatus based at least on the determined distribution of portion cuts and the determined location of defective areas.

Embodiment 3. A system according to embodiment 1 or 2, wherein the controller is configured to define at least a first defect level threshold defining a measure of the number and/or size of defects tolerable for a given type of food item.

Embodiment 4. A system according to embodiment 3, wherein the food item portions of the distribution comprise at least a first group and a second group, the first group comprising food item portions having a determined defect level below the first threshold, and the second group comprising food item portions having a determined defect level above the first threshold, and wherein the size of the items in the second group are determined based on the desired portion size and/or weight of portions in the first group.

Embodiment 5. A system according to any of the preceding embodiments, wherein the imaging system is arranged upstream of the cutting device.

Embodiment 6. A system according to any of the preceding embodiments, wherein the imaging system is configured to detect a colour distribution of the food item, and the controller is configured to determine the location of the defective areas based on at least the colour distribution.

Embodiment 7. A system according to any of the preceding embodiments, wherein the controller is configured to determine a two-dimensional weight distribution of the food item, the two-dimensional weight distribution extending in a plane parallel to a supporting conveyor surface of the conveyor, and to determine the distribution of portion cuts on the basis of the determined weight distribution of the food item.

Embodiment 8. A system according to embodiment 7, wherein the controller is configured to determine a three-dimensional surface profile of the food item on the basis of at least data received from the imaging system, and wherein the two-dimensional weight distribution is determined at least on the basis of the three-dimensional surface profile.

Embodiment 9. A system according to embodiment 7 or 8, wherein the controller is configured to determine a two- or three-dimensional density profile of the food item, and to determine the two-dimensional weight distribution of the food item on the basis of at least the determined density profile.

Embodiment 10. A method of cutting a food item into food item portions by use of a food processing system, the food processing system comprising a conveyor, an imaging system, a cutting device, and a controller, the method comprising the steps of:
the conveyor conveying the food item past the imaging system;
the imaging system imaging the food item and obtaining image data thereof;

the controller:
receiving the imaging data;
determining the location of defective areas on the basis of at least the received data; and
determining a distribution of portion cuts over the food item dividing the food item into food item portions on the basis of at least the determined location of defective areas and a desired portion size and/or weight;
the cutting device cutting the food item according to the determined distribution of portion cuts.

The invention claimed is:

1. A method of cutting a food item into food item portions by taking defective areas of the food item into consideration, the method comprising the steps of:
receiving imaging data of the food item;
determining one or more locations of defective areas in and/or on the food item based on at least the received data;
determining a distribution of food item portion cuts over the food item dividing the food item into food item portions based on at least the determined location of defective areas and at least one food portion feature;
transporting the food item to a cutting plane defined between a first conveyor belt and a second conveyor belt, the cutting plane being transverse to a transporting direction along the first conveyor belt and the second conveyor belt;
using a cutting device located in cutting plane and according to the determined distribution of food item portion cuts, cutting the food item into food item portions both along an entire width of the food item and outside of the defective areas of the food item when passing from the first conveyor belt to the second conveyor belt to create defect-containing pieces of the food item and defect-free portions of the food item; and
sorting out the defect-containing pieces of the food item by moving at least one of the conveyor belts away from the other conveyor belt to make a short-term opening between the first conveyor belt and the second conveyor belt for the defect-containing pieces of the food item to pass through the short-term opening.

2. The method according to claim 1, wherein defective areas comprise undesired parts which are not inherently expected in the type of food items to be cut.

3. The method according to claim 1, wherein a defective area comprises a part with a bruise, worm, nematode, blood spot, gaping texture, melanosis (melanin spots) and/or haematoma (blood clot).

4. The method according to claim 1, wherein in determining a distribution of food item portion cuts over the food item, food item portion cuts are determined close to located defective areas.

5. The method according to claim 1, wherein in the step of determining a distribution of food item portion cuts over the food item, food item portion cuts can be determined in areas without defective areas and which cuts are further determined on the basis of at least one portion feature.

6. The method according to claim 1, further comprising a step of determining a three-dimensional surface profile of the food item at least partly on the basis of the received data.

7. The method according to claim 1, further comprising a step of determining total weight, weight distribution and/or density distribution of the food item at least partly on the basis of the received data.

8. The method according to claim 7, wherein determining weight distribution is determining a two-dimensional weight distribution of the food item, the two-dimensional weight distribution extending in a plane parallel to a supporting conveyor surface of the conveyor, and further determining the distribution of food item portion cuts on the basis of the determined weight distribution of the food item.

9. The method according to claim 8, wherein the two-dimensional weight distribution is determined based on at least the three-dimensional surface profile.

10. The method according to claim 7, further comprising determining a two- or three-dimensional density profile of the food item and determining a two-dimensional weight distribution of the food item on the basis of at least the determined density profile.

11. The method according to claim 1, wherein the at least one food item portion feature is selected from the group of: portion size, portion weight, portion shape, portion color, portion color distribution, portion meat texture and/or portion meat-fat ratio.

12. The method according to claim 1, further comprising a step of sorting the cut food item portions,
wherein the sorting is based at least on the determined distribution of food item portion cuts and the determined location of defective areas.

13. The method according to claim 1, further comprising a step of detecting a color distribution of the food item and determining the location of the defective areas based on at least the color distribution.

14. The method according to claim 1, further comprising a step of defining at least a first defect level threshold defining a measure of the number and/or size of defects tolerable for a given type of food item.

15. The method according to claim 14, further comprising a step of determining at least a first group and a second group of the food item portions of the distribution, the first group comprising food item portions having a determined defect level below the first threshold, and the second group comprising food item portions having a determined defect level above the first threshold; and
wherein the size of the food item portions in the second group are determined based on the desired portion size and/or weight of food item portions in the first group.

16. The method according to claim 1, wherein the food item is from fish, poultry, pig, or cattle.

17. The method according to claim 16, wherein the food item is from fish, such as from salmon, trout, tilapia, cod, whiting, haddock, hake, pollock.

18. The method according to claim 17, wherein the food item is fillets, such as salmon fillets.

19. Use of a food processing system for performing the method of claim 1.

20. The use according to claim 19, wherein, the food processing system comprises at least one conveyor, an imaging system, a cutting device, and a controller, wherein:
the conveyor is configured for conveying the food item past the imaging system;
the imaging system is configured for imaging the food item and obtaining image data thereof;
the controller is arranged for:
receiving the imaging data;
determining the location of defective areas on the basis of at least the received data; and
determining a distribution of portion cuts over the food item dividing the food item into food item portions on the basis of at least the determined location of defective areas and a desired portion size and/or weight; and
the cutting device is configured for cutting the food item according to the determined distribution of portion cuts.

21. The use according to claim 20, wherein the processing system further comprises at least one sorting apparatus arranged downstream of the cutting device, and
wherein the controller is configured to control the sorting apparatus based at least on the determined distribution of portion cuts and the determined location of defective areas.

* * * * *